US009581549B2

(12) United States Patent
Raz et al.

(10) Patent No.: US 9,581,549 B2
(45) Date of Patent: Feb. 28, 2017

(54) NUCLEIC ACID TARGET DETECTION USING A DETECTOR, A PROBE AND AN INHIBITOR

(75) Inventors: Tal Raz, Cambridge, MA (US); Pascaline Mary, Cambridge, MA (US)

(73) Assignee: GnuBio, Inc., Cambridge, MA (US)

(*) Notice: Subject to any disclaimer, the term of this patent is extended or adjusted under 35 U.S.C. 154(b) by 111 days.

(21) Appl. No.: 13/992,187

(22) PCT Filed: Dec. 7, 2011

(86) PCT No.: PCT/US2011/063654
§ 371 (c)(1),
(2), (4) Date: Jun. 6, 2013

(87) PCT Pub. No.: WO2012/078710
PCT Pub. Date: Jun. 14, 2012

(65) Prior Publication Data
US 2013/0344485 A1    Dec. 26, 2013

Related U.S. Application Data

(60) Provisional application No. 61/420,747, filed on Dec. 7, 2010.

(51) Int. Cl.
C12Q 1/68       (2006.01)
C12P 19/34      (2006.01)
G01N 21/64      (2006.01)

(52) U.S. Cl.
CPC ....... *G01N 21/6486* (2013.01); *C12Q 1/6818* (2013.01); *C12Q 1/6858* (2013.01)

(58) Field of Classification Search
CPC .................................. C12Q 1/68; C07H 21/00
USPC ................. 435/6.1; 536/22.1, 23.1, 24.3
See application file for complete search history.

(56) References Cited

U.S. PATENT DOCUMENTS

| | | | |
|---|---|---|---|
| 6,007,994 A * | 12/1999 | Ward et al. .................. | 435/6.11 |
| 7,081,336 B2 * | 7/2006 | Bao et al. ..................... | 435/6.11 |
| 8,528,589 B2 | 9/2013 | Miller et al. | |
| 8,535,889 B2 | 9/2013 | Larson et al. | |
| 2001/0039039 A1 * | 11/2001 | Weissman ........... | C12Q 1/6827 435/91.1 |
| 2003/0148303 A1 * | 8/2003 | Nadeau et al. .................. | 435/6 |
| 2008/0014589 A1 | 1/2008 | Link | |
| 2010/0129792 A1 | 5/2010 | Makrigiorgos | |
| 2010/0273156 A1 * | 10/2010 | Hellyer et al. ..................... | 435/6 |
| 2011/0151578 A1 | 6/2011 | Abate et al. | |
| 2011/0218123 A1 | 9/2011 | Weitz et al. | |
| 2011/0250597 A1 | 10/2011 | Larson et al. | |
| 2011/0267457 A1 | 11/2011 | Weitz et al. | |
| 2012/0015822 A1 | 1/2012 | Weitz et al. | |
| 2012/0132288 A1 | 5/2012 | Weitz et al. | |
| 2012/0219947 A1 | 8/2012 | Yurkovetskty et al. | |
| 2012/0220494 A1 | 8/2012 | Samuels et al. | |
| 2012/0222748 A1 | 9/2012 | Weitz et al. | |
| 2012/0309002 A1 | 12/2012 | Link | |

FOREIGN PATENT DOCUMENTS

| | | |
|---|---|---|
| EP | 2364774 A2 | 9/2011 |
| EP | 2662135 A2 | 11/2013 |
| WO | 96/15720 A1 | 5/1996 |
| WO | 2007/081385 A2 | 7/2007 |
| WO | 2007/081387 A1 | 7/2007 |
| WO | 2008/021446 A2 | 2/2008 |
| WO | 2012/135201 A1 | 10/2012 |
| WO | 2012/135259 A1 | 10/2012 |
| WO | 2012/135327 A1 | 10/2012 |
| WO | 2013/095737 A2 | 6/2013 |
| WO | 2013/122826 A1 | 8/2013 |
| WO | 2013/165748 A1 | 11/2013 |
| WO | 2014/043388 A1 | 3/2014 |
| WO | 2014/093976 A1 | 6/2014 |
| WO | 2014117088 A1 | 7/2014 |

OTHER PUBLICATIONS

Barany, F. Genetic disease detection and DNA amplification using cloned thermostable ligase. PNAS 88 (1) :189 (1991).*
Gullberg et al., Cytokine detection by antibody-based proximity ligation. PNAS 101 (22) : 8420 (2004).*
Kong et al. Duplex probes: a new approach for the detection of specific nucleic acids in homogenous assays. Analytica Chimica Acta 491 :135 (2003).*
Lee, H. Ligase Chain Reaction 24 : 197 (1996).*
Wiedmann et al. Ligase chain reaction (LCR)—overview and applications. PCR Methods and Applications 3: S51-S64 (1994).*
U.S. Appl. No. 14/290,867, filed May 29, 2014.
U.S. Appl. No. 14/289,982, filed May 29, 2014.
U.S. Appl. No. 14/470,860, filed Aug. 27, 2014.
U.S. Appl. No. 14/502,948, filed Sep. 30, 2014.
International Appl. No. PCT/US2014/035730, filed Apr. 28, 2014, in the name of GnuBio, Inc.
Livak et al., "Oligonucleotides with fluorescent dyes at opposite ends provide a quenched probe system useful for detecting PCR product and nucleic acid hybridization", *PCR Methods & Applications* 1995, 4(6):357-362.
Yang et al., "A novel universal real-time PCR system using the attached universal duplex probes for quantitative analysis of nucleic acids", *BMC Molecular Biology*, 2008, vol. 9, No. 1, 13 pages.
Extended European Search Report from EP Application No. 11846231.6, dated Apr. 30, 2015 (6 pages).

* cited by examiner

*Primary Examiner* — Ethan C Whisenant
(74) *Attorney, Agent, or Firm* — Kilpatrick Townsend & Stockton LLP

(57) ABSTRACT

The present invention generally pertains to methods for detecting the presence or absence of a particular nucleic acid sequence. The present invention generally relates to incorporating a detector into a target nucleic acid, adding an oligonucleotide probe, polymerase enzyme and an inhibitor to the reaction, and detecting interference of the oligonucleotide probe with the inhibitor as an indication of the presence of a particular target nucleic acid sequence as well as kits encompassing the same.

20 Claims, 11 Drawing Sheets

FIG. 1B – MISMATCHED PROBE

FIG. 1A – MATCHED PROBE

FIG. 2A – MATCHED PROBE

FIG. 2B – MISMATCHED PROBE

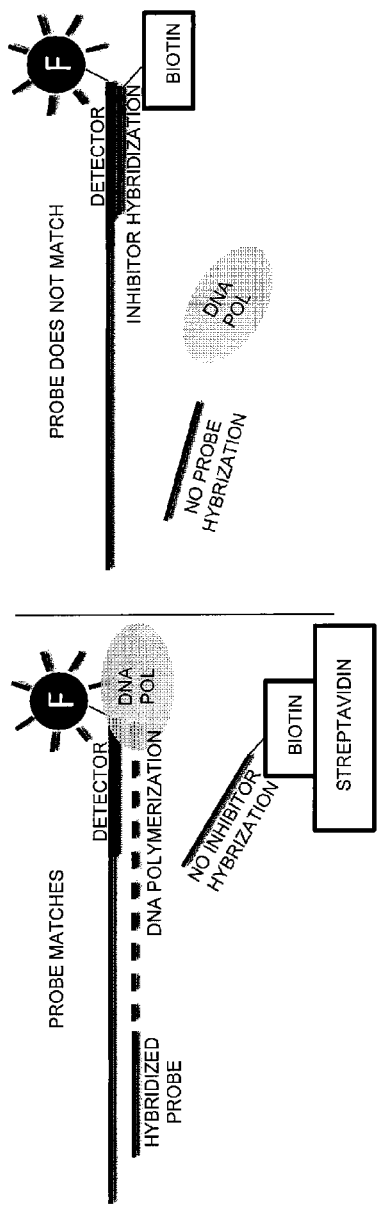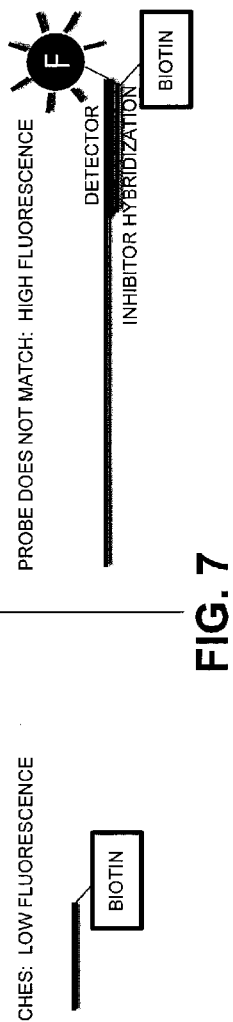
FIG. 7

| | |
|---|---|
| Matched | CGCATATG |
| Mismatched 1 | CGCATATC |
| Mismatched 2 | CGCATAGG |
| Mismatched 3 | CGCATCTG |
| Mismatched 4 | CGCAGATG |
| Mismatched 5 | CGCCTATG |
| Mismatched 6 | CGGATATG |

FIG. 8

NUCLEIC ACID TARGET DETECTION USING A DETECTOR, A PROBE AND AN INHIBITOR

RELATED APPLICATIONS AND INCORPORATION BY REFERENCE

This application is a national phase application under 35 USC §371 of PCT Application No. PCT/US2011/063654 filed Dec. 7, 2011, which claims the benefit of priority claims priority to U.S. provisional patent application Ser. No. 61/420,747 filed Dec. 7, 2010, the teaching and contents of which are hereby incorporated by reference.

FEDERAL FUNDING LEGEND

This invention was supported, in part, by National Institutes of Health grant number: 1R43HG005144-01. The federal government may have certain rights to this invention.

The foregoing application, and all documents cited therein or during its prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

This application contains a sequence listing in computer readable format, the teachings and content of which are hereby incorporated by reference.

FIELD OF THE INVENTION

The present invention is in the technical field of biotechnology. More particularly, the present invention is in the technical field of molecular biology.

BACKGROUND OF THE INVENTION

In most processes within molecular biology it is critical to have a reaction that takes into account the ability to detect the occurrence of a particular event. For instance, events such as the incorporation of one, or many, nucleotides onto an extension primer may be indicative of the presence of a single nucleotide polymorphism. Upon the occurrence of an event, such as the incorporation of one or more nucleotides, a mechanism for detection may be built into the reaction or, alternatively, used in a subsequent reaction to provide a means to signal the occurrence of the event.

Single base chain extension, whereby the incorporation of a single di-deoxy nucleotide, which may contain a dye for detection (or use mass as a means for detection), is an example of a reaction that contains both an interrogation and a detection mechanism for nucleic acids. One of the simplest ways to detect a single nucleotide extension is by fluorescence, for example, by using fluorescently labeled nucleotides or a FRET (fluorescence resonance energy transfer) signal. However, single base chain extension is costly because it requires the use of fluorescently labeled nucleotides, and/or probes. Additionally, the concentration of both the probes and the nucleotides must be high for the reaction to work, resulting in a high background signal. Consequently, multiple rigorous wash steps must be employed to remove the unhybridized or unbound material, which is not practical for most applications, particularly when using small reaction vessels.

Another rendition of fluorescence-based detection is the utilization of a fluorescently tagged molecule (a fluorophore) and a quencher. As described above, when working with a plurality of molecules, the concentration of the fluorescence molecules may be problematic in terms of signal.

One solution to this problem is the use of double stranded fluorescence-quencher probes. Such assays are often optimized for specific parameters such as probe length, target DNA length, or enzymatic reaction. Most fluorophore-quencher pair assays are effective only for short DNA strands or amplicons (<200 bp) under tight thermal control (e.g., Holland et al., "Detection of specific polymerase chain reaction product by utilizing the 5'→3' exonuclease activity of *Thermus aquaticus* DNA polymerase", *PNAS* (1991) vol. 88, pp. 7276-7280; Piatek, et al., "Molecular beacon sequence analysis for detecting drug resistance in *Mycobacterium tuberculosis*", Nat Biotechnol (1998) vol. 16, no. 4, pp. 359-363; Udvardi, et al., "Eleven golden rules of quantitative RT-PCR", *The Plant Cell* (2008) vol. 20, pp. 1736-1737; Vet al., "Design and Optimization of Molecular Beacon Real-Time Polymerase Chain Reaction Assays", In: P. Herdewijn, ed. 2004. *Oligonucleotide Synthesis: Methods and Applications* (Methods in Molecular Biology, vol. 288). New Jersey: Humana Press Inc., pp. 273-290; "Top Ten Pitfalls in Quantitative Real-time PCR Primer/Probe Design and Use", Applied Bio systems TechNotes (2011) vol. 13, no. 4 (www.ambion.com/techlib/tn/134/13.html); "PCR Primer Design Guidelines", PREMIERBiosoft (2011) (www.premierbiosoft.com/tech_notes/PCR_Primer_Design.html).

Accordingly, there is a need for a reliable, efficient and cost-effective method for detecting the presence or absence of a particular nucleic acid sequence using a variety of nucleic acid probe lengths, target nucleic acid lengths, temperature conditions or DNA polymerases, as provided by the following invention.

Citation or identification of any document in this application is not an admission that such document is available as prior art to the present invention.

SUMMARY OF THE INVENTION

The present invention generally pertains to methods for detecting the presence or absence of a particular nucleic acid sequence. One method according to the invention pertains to incorporating a detector into a target nucleic acid, adding an oligonucleotide probe, polymerase enzyme and an inhibitor to the reaction, and detecting interference of the oligonucleotide probe with the inhibitor as an indication of the presence of a particular target nucleic acid sequence. The lack of interference is an indication of the absence of a particular nucleic acid sequence.

The present invention also pertains to a method for detecting a target nucleic acid sequence in a nucleic acid sample within an emulsion. This method pertains to incorporating a detector into the target nucleic acid, adding an oligonucleotide probe, polymerase enzyme and an inhibitor to the reaction, and detecting interference of the oligonucleotide probe with the inhibitor as an indication of the presence of a particular target nucleic acid sequence, and wherein the reaction takes place within an emulsion. The lack of interference is an indication of the absence of a particular nucleic acid sequence.

The present invention also pertains to a method for detecting a target nucleic acid in a nucleic acid sample in a microfluidic device. This method pertains to incorporating a detector into the target nucleic acid, adding an oligonucleotide probe, polymerase enzyme and an inhibitor to the reaction, and detecting interference of the oligonucleotide probe with the inhibitor as an indication of the presence of a particular target nucleic acid sequence, wherein the reaction takes place within a microfluidic device. The lack of interference is an indication of the absence of a particular nucleic acid sequence.

The present invention also pertains to a kit containing the reagents for a method for detecting a target nucleic acid sequence in a nucleic acid sample. The kit may comprise a detector for incorporation into the target nucleic acid, an oligonucleotide probe, polymerase enzyme and an inhibitor to the reaction, together with reagents for detecting interference of the oligonucleotide probe with the inhibitor, as an indication of the presence of a particular target nucleic acid sequence. The kit may further contain the reagents for performing the methods of this invention.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1A depicts an oligonucleotide probe that matches the target nucleic acid acting as a primer for DNA polymerization. The resulting double stranded DNA blocks the binding site for inhibitor on the detector, resulting in fluorescent signal. FIG. 1B depicts an oligonucleotide probe that does not match the target nucleic acid. Therefore, the inhibitor binds to the detector and quenches the fluorescent signal. F is a fluorescent label (i.e., a detector-fluorophore conjugate) and Q is a quencher (i.e., an inhibitor-quencher conjugate).

FIG. 7 is a schematic illustrating the example where the detector may comprise a fluorophore and the inhibitor is conjugated to biotin ("inhibitor-biotin conjugate").

FIG. 8 is an illustration of the nucleotide match and mismatch positions of the oligonucleotide probes used in Example 1.

DETAILED DESCRIPTION OF THE INVENTION

Figure 1:
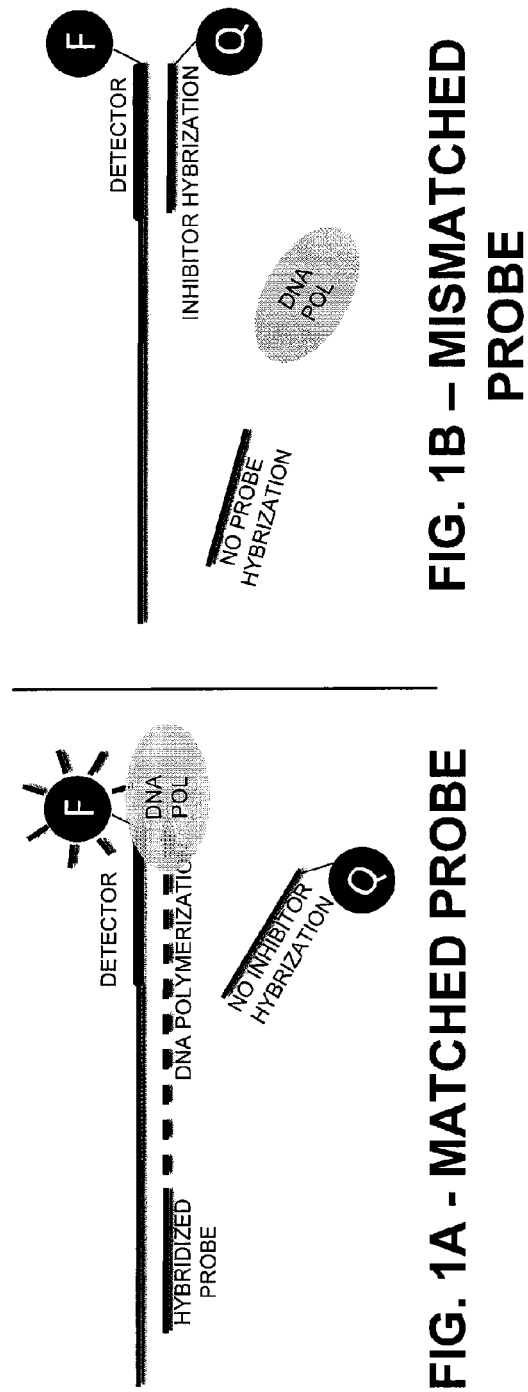
FIGS. 1A and 1B are schematics showing the reaction in use to detect a target nucleic acid, wherein the detector is conjugated to a fluorophore and the inhibitor is conjugated to a quencher.

The present invention generally pertains to methods for detecting the presence or absence of a particular nucleic acid sequence, referred to herein as the "target nucleic acid". The target nucleic acid is the nucleic acid sample being queried after having been obtained from a human or animal and includes, but is not limited to, genomic DNA, PCR amplicon, cDNA, and others. The target nucleic acid may be double stranded or single stranded. In one example, the single stranded target nucleic acid is DNA. In one embodiment, a double stranded target nucleic acid is first converted to a single stranded target nucleic acid. In yet another embodiment, PCR is performed on the target nucleic acid prior to detection. In one aspect of this embodiment, the PCR product is subsequently converted to single stranded form. Methods for converting a double stranded nucleic acid into a single stranded nucleic acid are known in the art and are described, for example, by Mitsis et al., "Characterization of the interaction of lambda exonuclease with the ends of DNA", *Nucleic Acids Res* (1999) vol. 27, no. 15, pp. 3057-3063; Sanchez, et al., "Linear-After-The-Exponential (LATE)-PCR: An advanced method of asymmetric PCR and its uses in quantitative real-time analysis", *PNAS* (2004) vol. 101, no. 7, pp. 1933-1938; Chen, et al., "Asynchronous PCR", In: D. Park, ed. 2011. *PCR Protocols* (Methods in Molecular Biology, vol. 687). New Jersey: Humana Press Inc., pp. 231-243.

The methods of the invention may be used to detect the presence or absence of a nucleic acid sequence within a target nucleic acid. In one embodiment, a single nucleotide within the target nucleic acid sequence is detected. In one aspect of this embodiment, a particular locus may be queried to detect the presence or absence of a particular nucleic acid sequence variance. A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances, i.e., two or more nucleotide additions, deletions and/or substitutions in the same polynucleotide. A "point mutation" refers to a single substitution of one nucleotide for another.

For example, a particular locus may be queried to detect the presence or absence of a single nucleotide polymorphism. A "single nucleotide polymorphism" or "SNP" refers to a variation in the nucleotide sequence of a polynucleotide that differs from another polynucleotide by a single nucleotide difference. A SNP included, for example and without limitation, exchanging one A for one C, G or T, or one C for one G, T or C and so on, in the entire sequence of polynucleotide. Additionally, it is possible to have more than one SNP in a particular nucleic acid sequence. For example, at one position in a nucleic acid sequence, a G may be exchanged for an A, at another position a C may be exchanged for a T and so on.

In another example, a particular locus may be queried to detect the presence or absence of a single nucleotide mutation. In another embodiment, a plurality of nucleotide targets (e.g., two or more nucleotides) is detected within the same reaction. In one aspect of this embodiment, a short nucleic acid sequence within the target nucleic acid sequence in detected. In one example, the nucleic acid probe is as short as about 6 to 8 nucleotides long. In another aspect of this embodiment, a full complement of short nucleic acid probes can be used sequentially to determine the entire sequence of the target nucleic acid. For example, the full complement of short nucleic acid probes may be a set of all 4096 possible hexamers. Accordingly, a target nucleic acid may be detected using the methods of this invention with no specific target length limitation.

The methods of this invention may further comprise the use of a detector that is incorporated into the target nucleic acid. The detector is an oligonucleotide incorporated into the target nucleic acid to function as a binding site for an inhibitor of the reaction. In one embodiment, the detector is incorporated into the target nucleic acid by ligation of adaptors. In one example of this embodiment, the adaptors are two oligonucleotides analogous to each other. In this example, the adaptors attach the detector to the target nucleic acid. In another embodiment, the detector is incorporated into the nucleic acid sample using PCR primers. In one example of this embodiment, the PCR primers include a target-specific sequence (on the 3' end of the primer), a universal nucleic-acid sequence designed to hybridize to the inhibitor in downstream steps (on the 5' end of the primer), and a detector. In any embodiment, the detector is incorporated into the target nucleic acid sequence and oriented 5' of the target nucleic acid sequence.

In one embodiment, the detector is conjugated to a fluorophore. The fluorophore is a molecule that has the ability to absorb energy from light of a specific wavelength, and then emit this energy as fluorescence in another specific wavelength characteristic for the particular fluorophore. In this manner, the fluorophore will facilitate the final assay readout indicating the presence or absence of a target nucleic acid. The particular fluorophore employed is not critical to the present invention. Fluorophores are known in the art and are described, for example, by Marras, "Selection of Fluorophore and Quencher Pairs for Fluorescent Nucleic Acid Hybridization Probes", In: V. Didenko, ed. 2006. *Fluorescent Energy Transfer Nucleic Acid Probes: Designs and Protocols* (Methods in Molecular Biology, vol. 335). New Jersey: Humana Press Inc., pp. 3-16. Examples of fluorophores that can be employed in the present invention include, but are not limited to, those described by Marras 2006 and further described herein below. The particular location of the fluorophore in relation to the detector is not critical to the present invention. The fluorophore can be attached anywhere along the detector, including the 5' end, the 3' end or anywhere internally along the detector.

The methods of the invention may further comprise the use of an inhibitor. The inhibitor is an oligonucleotide that is analogous to, and hybridizes with, the detector. The inhibitor functions to allow a signal to be detected only if an oligonucleotide probe matches the target nucleic acid. Hybridization of the inhibitor to the detector takes place in standard reaction buffer, for example, in a DNA polymerase reaction buffer whereby the detector and the inhibitor are mixed in the buffer at the appropriate temperature. In one example, the reaction may be heated to 95° C. for a period of 30 seconds and then chilled to 5° C. below the annealing temperature of the inhibitor.

In one embodiment, the inhibitor is conjugated to a quencher. The quencher is a molecule that functions to decrease, i.e., quench the intensity of the fluorescence by transferring energy from a first fluorophore to a second fluorophore or to a non-fluorescent molecule. The particular quencher employed is not critical to the present invention. Quenchers are known in the art and are described, for example by, Marras 2006. Examples of quenchers that can be employed in the present invention include, but are not limited to, those described by Marras 2006 and further described herein below. The particular location of the quencher in relation to the inhibitor is not critical to the present invention. The quencher can be attached anywhere along the inhibitor, including the 5' end, the 3' end or anywhere internally along the inhibitor.

In an alternative embodiment, the detector is conjugated to a quencher. The particular quencher employed is not critical to the present invention. Examples of quenchers that can be employed in the present invention include, but are not limited to, those described by Marras 2006 and further described herein below. The particular location of the quencher in relation to the detector is not critical to the present invention. The quencher can be attached anywhere along the detector, including the 5' end, the 3' end or anywhere internally along the detector.

In an alternative embodiment, the inhibitor is conjugated to a fluorophore. The particular fluorophore employed is not critical to the present invention. Examples of fluorophores that can be employed in the present invention include, but are not limited to, those described by Marras 2006 and further described herein below. The location of the fluorophore in relation to the inhibitor is not critical to the present invention. The fluorophore can be attached anywhere along the inhibitor, including the 5' end, the 3' end or anywhere internally along the inhibitor.

In another embodiment of the methods of this invention, the inhibitor is conjugated to biotin ("inhibitor-biotin conjugate"). Inhibitor-biotin conjugates can be obtained commercially from various vendors (e.g., Integrated DNA Technologies, Inc., Eurofins MWG Operon, Eurogentec, TriLink BioTechnologies, Inc.). Examples of commercially available purification kits include Agencourt®-AMPure® XP (Beckman Coulter, Inc.), and QIAquick 96 PCR Purification kit (Qiagen). The particular location of the biotin in relation to the inhibitor is not critical to the present invention. The biotin can be attached anywhere along the inhibitor, including the 5' end, the 3' end or anywhere internally along the inhibitor.

In another embodiment of the methods of this invention, the detector or the inhibitor is conjugated to a molecule that will facilitate isolation of the detector or the inhibitor, respectively, from the reaction. The molecule that will facilitate this isolation may be, for example, an epitope, which is anything capable of reacting with an antibody. The epitope may be, for example, an antigen, peptide or protein. In one example, the epitope is biotin.

In another embodiment of the methods of this invention, the detector or the inhibitor is conjugated to a molecule that will facilitate detection of the detector or the inhibitor, respectively, within the reaction. The molecule that will facilitate this detection may be, for example, an epitope. The epitope may be, for example, an antigen, peptide or protein. In one example, the epitope is biotin. In another example, the epitope is a peptide that can be detected using a chemiluminescent assay, e.g., by using secondary antibodies conjugated to the HRP enzyme.

In the above embodiments wherein the detector or the inhibitor is conjugated to biotin, the conjugation can be achieved by PCR amplification of the detector or the inhibitor with a biotin conjugated primer (commercially available from Integrated DNA Technologies, Inc., Operon, Eurogentec, and TriLink BioTechnologies, Inc.). In the above embodiments wherein the epitope is detected using antibodies conjugated to the HRP enzymes, conjugation kits may be obtained commercially from Solulink or the antibody-HRP enzyme conjugates may be ordered directly from commercial venders, e.g., Eurogentec).

In one embodiment of the methods of this invention, when the detector is conjugated to a fluorophore, the inhibitor is conjugated to a quencher. In another embodiment of the methods of this invention, when the detector is conjugated to a quencher, the inhibitor is conjugated to a fluorophore. The efficiency of energy transfer between the detector and the inhibitor or the inhibitor and the detector, respectively, is specific to the fluorophore-quencher pair chosen and should be optimized accordingly, as described by Marras 2006 and product literature provided by known commercial vendors listed herein below.

In another embodiment of the methods of this invention, the detector is conjugated to a first fluorophore and the inhibitor is conjugated to a second fluorophore, such that emission from the first fluorophore will excite the second fluorophore by energy transfer, and wherein the transferred energy is emitted as fluorescence characteristic of the second fluorophore. This quenching phenomenon is known in the art and described, for example, by Marras 2006. Fluorophore-fluorophore pairs are also known in the art and are described, for example by, Marras 2006. Examples of fluorophore-fluorophore pairs that can be employed in the present invention include, but are not limited to, those described by Marras 2006 and further described herein below. The particular location of the first fluorophore in relation to the detector and the second fluorophore in relation to the inhibitor in is not critical to the present invention. The first fluorophore can be attached anywhere along the detector, including the 5' end, the 3' end or anywhere internally along the detector. The second fluorophore can be attached anywhere along the inhibitor, including the 5' end, the 3' end or anywhere internally along the inhibitor. The efficiency of energy transfer between the detector and inhibitor is specific to the fluorophore-fluorophore pairs chosen and should be optimized accordingly.

The fluorophore and quencher of a fluorophore-quencher pair or the first fluorophore and second fluorophore of a fluorophore-fluorophore pair (referred to individually and collectively as "FRET pair(s)") may be placed anywhere in relation to each other as long as the distance ("FRET distance") does not fall beyond the efficient energy transfer distance of the particular FRET pair. The importance of FRET distance is known in the art and is described, for example, by Marras 2006. The efficiency of energy transfer between the detector and the inhibitor is specific to the FRET pair chosen and should be optimized accordingly.

Figure 3:
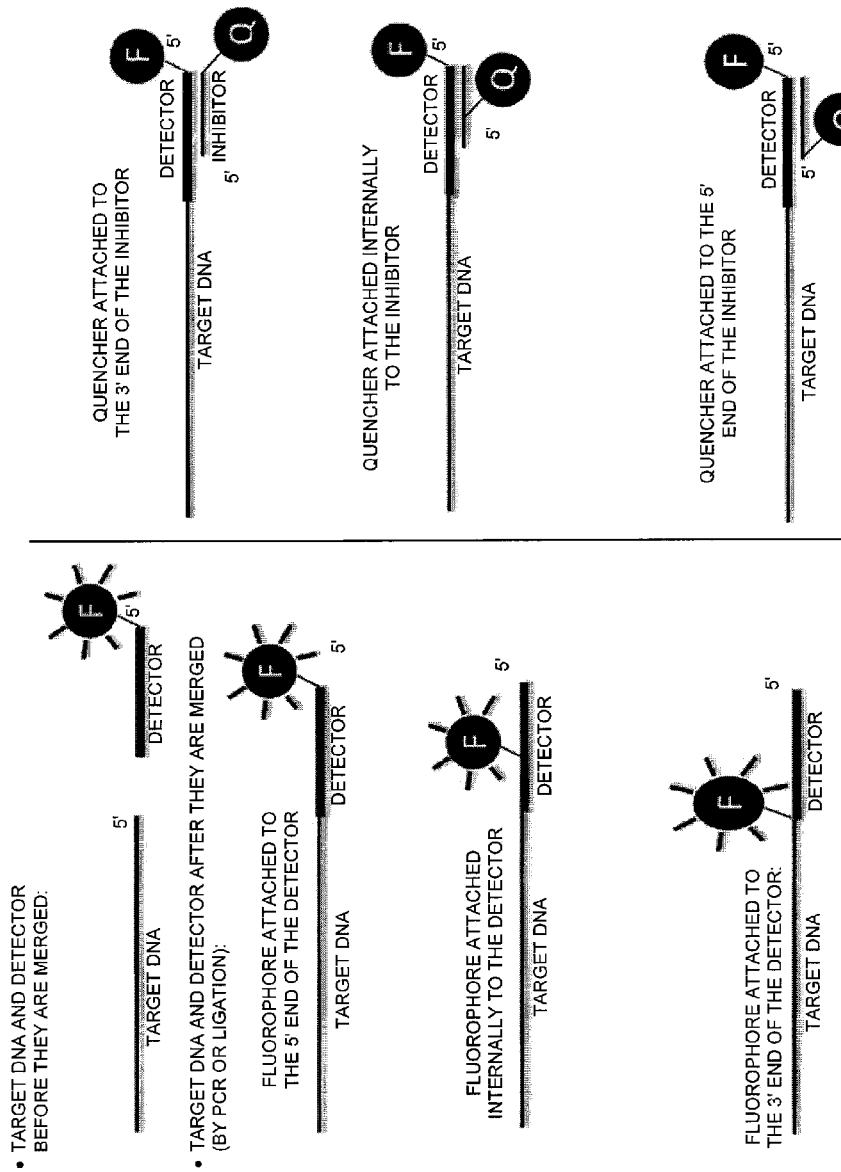
FIG. 3 is a schematic illustrating various positions of the fluorophore on the detector and the quencher on the inhibitor.
Figure 4:
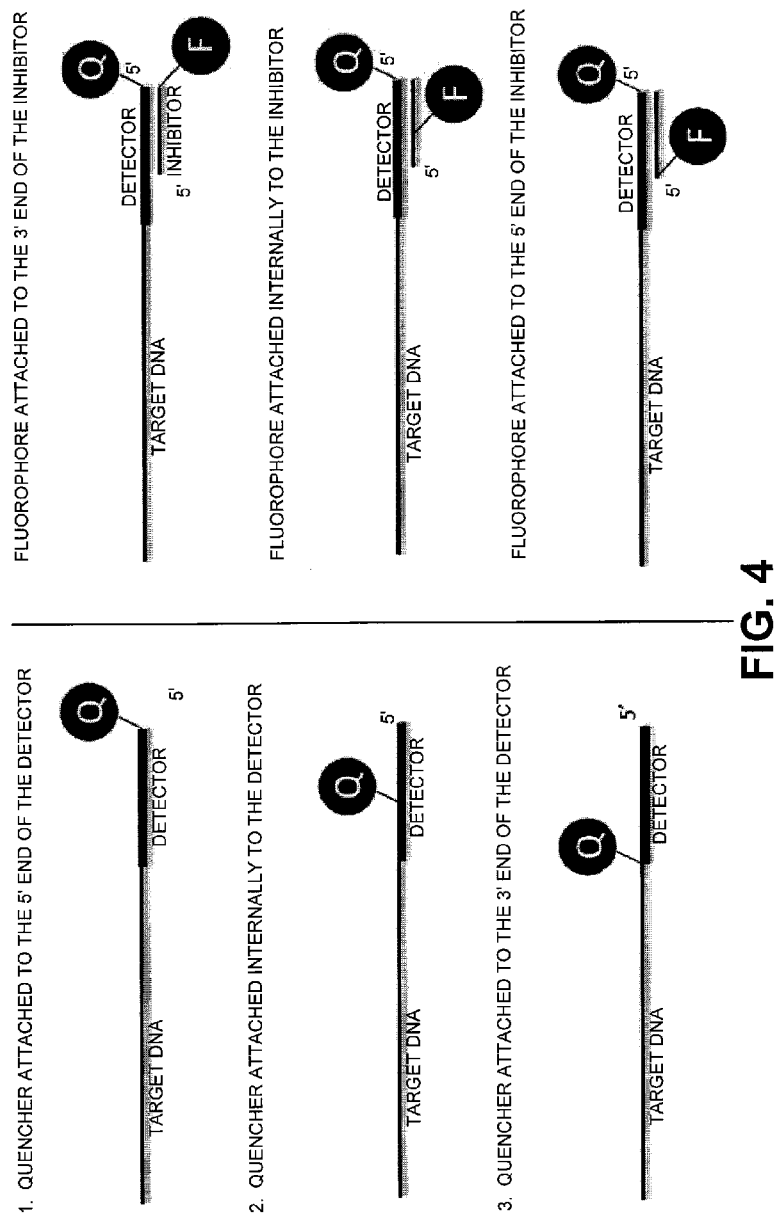
FIG. 4 is a schematic illustrating various positions of the quencher on the detector and the fluorophore on the inhibitor.

As illustrated in FIG. 3, the fluorophore can be located anywhere on the detector and the quencher can be located anywhere on the inhibitor, as long as they are within FRET distance of each other. Alternatively, as illustrated in FIG. 4, the quencher can be located anywhere on the detector and the fluorophore can be located anywhere on the inhibitor as long as they are within FRET distance of each other. Thus, the fluorophore and the quencher must be within an acceptable FRET distance to each other that allows the reaction to occur. This FRET distance is particular to the fluorophore-quencher pair chosen and each fluorophore and quencher can be on adjacent nucleotides, tens of nucleotides apart or even hundreds of nucleotides apart, depending on the particular FRET pair chosen.

In one example, the fluorophore is on the 5' end of the detector and the quencher is on the 3' end of the inhibitor. In another example, the quencher is on the 5' end of the detector and the fluorophore is on the 3' end of the inhibitor.

Figure 5:
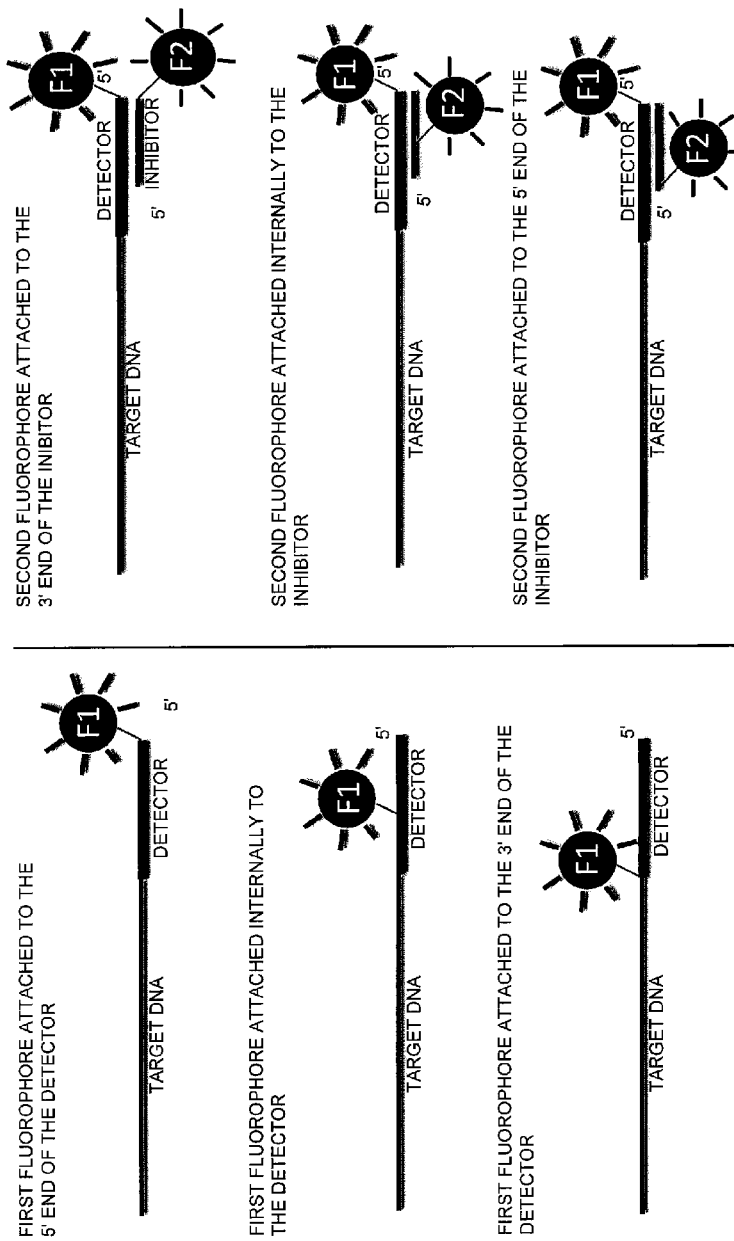
FIG. 5 is a schematic illustrating various positions of the first fluorophore on the detector and the second fluorophore on the inhibitor.

As illustrated in FIG. 5, the first fluorophore can be located anywhere on the detector and the second fluorophore can be located anywhere on the inhibitor, as long as they are within FRET distance of each other. Thus, the first fluorophore and the second fluorophore must be within an acceptable distance to each other that allows the reaction to occur. This FRET distance is particular to the fluorophore-fluorophore pair and each fluorophore can be on adjacent nucleotides, tens of nucleotides apart or even hundreds of nucleotides apart, depending on the particular FRET pair chosen.

In one example, the detector is conjugated to a FAM fluorophore on its 5' end and the inhibitor is conjugated to a TAMRA fluorophore positioned approximately 15 nt away from the FAM fluorophore.

The selection of a particular fluorophore-quencher or fluorophore-fluorophore pair is not critical. Examples of the categories of fluorophores that can be employed in the present invention include, but are not limited to adjacent probes (e.g., LightCycler® hybridization probes, available from Sigma-Aldrich®), 5'-nuclease probes (or TaqMan® probes, available from PREMIER Biosoft)), minor groove binder (Taqman® MGB probes, available from Applied Biosystems®) proves, molecular beacon probes, Scorpions® primers (available from PREMIER Biosoft and Biosearch Technologies), and strand-displacement probes (or Yin-Yang probes).

Examples of the specific fluorophores that may be employed in the present invention include, but are not limited to fluorescein and derivatives thereof (e.g., fluorescein isothianate (FITC), carboxyfluorescein (FAM), tetrachlorofluorescein (TET), 2',7'-difluorofluorescein (Oregon Green® 488), Oregon Green® 514 carboxylic acid, and a fluorescein with chloro and methoxy substituents (JOE and 6-JOE)); rhodamine derivatives (e.g., tetramethyl rhodamine (TAMRA), tetramethyl rhodamine iso-thiocyanate (TRITC), tetramethylrhodamine (TMR), carboxy-X-rhodamine (ROX), Texas Red (a mixture of isomeric sulfonyl chlorides and sulforhodamine; Invitrogen™) and Texas Red-X (Texas Red succinimidyl ester, which contains an additional seven-atom aminohexanoyl spacer ("X") between the fluorophore and its reactive group; Invitrogen™), and Rhodamine X); cyanine (Cy) dyes (e.g., Cy3, Cy5 and Cy5.5) and cyanine derivatives (e.g., indocarbocyanine (Quasar® 570, Quasar® 670 and Quasar® 705), Oregon Green® isothiocyanate, and eosin isothiocyanate (EITC)); N-hydroxysuccinimidyl 1-pyrenebutyrate (PYB); N-hydroxysuccinimidyl 1-pyrenesulfonate (PYS); (5-(2'-aminoethyl)aminonaphthalene (EDANS); CAL Fluor® Gold 540, CAL Fluor® Orange 560, Fluor® Red 590, CAL Fluor® Red 610, and CAL Fluor® Red 635 (proprietary fluorophores available from Biosearch Technologies, Inc.); VIC®; HEX® (a 6-isomer phosphoramidite); and NED®.

Examples of the specific quenchers that may be employed in the present invention include, but are not limited to Black Hole Quencher® dyes (BHQ®-1, BHQ®-2, BHQ®-3); ρ-(dimethyl aminophenylazo)benzoic acid (DABCYL); Deep Dark Quencher DDQ-I (Eurogentec); Eosin(2',4',5',7'-tetrabromofluorescein); Eclipse® Dark Quencher (Eurogentec); Iowa Black® Quenchers, e.g., Iowa Black® FQ and Iowa Black® RQ (Integrated DNA Technologies, Inc.); QSY-7, QSY-9 and QSY-21 (Molecular Probes®).

Examples of specific fluorophore-quencher pairs that may be employed in the present invention include, but are not limited to, fluorescein/DABCYL, EDANS/DABCYL, CAL Fluor® Gold 540/BHQ®-1, Cy3/BHQ-1, FAM/BHQ®-1, TET/BHQ®-1, JOE/BHQ®-1, HEX/BHQ®-1, Oregon Green®/BHQ-1, Cy3/BHQ®-2, Cy5/BHQ-2, ROX/BHQ®-2, TAMRA/BHQ-2, Cy5/BHQ®-3, and Cy5.5/BHQ®-3.

Examples of specific fluorophore-fluorophore pairs that may be employed in the present invention include, but are not limited to, FAM/TAMRA, FITC/TAMRA, FITC/Rhodamine X, PYS/FITC, FITC/EITC, FITC/PYB, FITC/Texas Red, and FITC/TRITC.

The methods of the invention may further comprise the use of an oligonucleotide probe that functions as a query molecule looking for a match to a sequence (the "query sequence") in the target nucleic acid. If the oligonucleotide probe matches the target nucleic acid, it hybridizes to it and acts as a primer for nucleic acid polymerase chain extension. As the extension proceeds, it will displace the inhibitor from the detector. If the oligonucleotide probe does not match the target nucleic acid, it will not hybridize to the target nucleic acid and no chain extension will occur, allowing the inhibitor to remain attached to the detector.

The methods of the invention may further comprise the use of a polymerase enzyme. This may be any enzyme with strand-displacement capacity. Examples of commercially available polymerase enzymes include, but are not limited to: Klenow fragment (New England Biolabs® Inc.), Taq DNA polymerase (QIAGEN), 9°N™ DNA polymerase (New England Biolabs® Inc.), Deep Vent™ DNA polymerase (New England Biolabs® Inc.), Manta DNA polymerase (Enzymatics®), Bst DNA polymerase (New England Biolabs® Inc.), and phi29 DNA polymerase (New England Biolabs® Inc.).

In one embodiment of the methods of this invention, the detector is conjugated to a fluorophore and the inhibitor is conjugated to a quencher. In this example, the detector is incorporated into the target nucleic acid, followed by addition of an oligonucleotide probe, a polymerase and an inhibitor to the reaction. The fluorophore emits fluorescence until the inhibitor binds to the detector and quenches the fluorescent signal by way of the quencher. If the oligonucleotide probe finds a match in the target nucleic acid (as illustrated in FIG. 1A), the polymerase will extend the probe until it reaches the inhibitor and displaces the inhibitor from the detector. As a result, the quencher no longer quenches the fluorescence emitted by the fluorophore and a relatively strong fluorescent signal is emitted. If the oligonucleotide probe does not find a match in the target nucleic acid (as illustrated in FIG. 1B), the inhibitor will remain in place and the quencher will continue to quench the fluorescence emitted by the fluorophore, resulting in a continued relatively low fluorescent signal.

Figure 2:
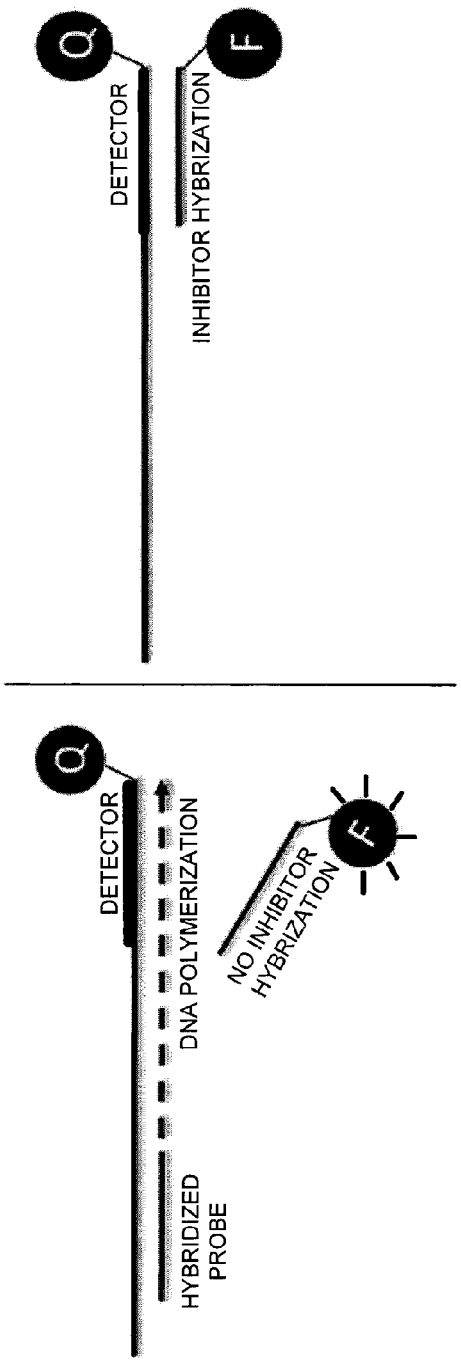
FIG. 2 is a schematic showing the reaction in use to detect a target nucleic acid, where the detector is conjugated to a quencher and the inhibitor is conjugated to a fluorophore.

In another embodiment of the methods of this invention, the detector is conjugated to a quencher and the inhibitor is conjugated to a fluorophore. In this example, the detector is incorporated into the target nucleic acid, followed by addition of an oligonucleotide probe, a polymerase and an inhibitor to the reaction. The inhibitor binds to the detector and the fluorescence emitted by the fluorophore is quenched by the quencher of the detector. If the oligonucleotide probe finds a match in the target nucleic acid, the polymerase will extend the probe until it reaches the inhibitor and displaces the inhibitor from the detector (as illustrated in FIG. 2A). As a result, the quencher no longer quenches the fluorescence emitted by the fluorophore and a relatively strong fluorescent signal is emitted. If the oligonucleotide probe does not find a match in the target nucleic acid (as illustrated in FIG. 2B), the inhibitor will remain in place and the quencher will continue to quench the fluorescence emitted by the fluorophore, resulting in continued relatively low fluorescent signal.

In another aspect of this embodiment, the detector is conjugated to a first fluorophore and the inhibitor is conjugated to a second fluorophore. In this example, the detector is incorporated into the target nucleic acid, followed by addition of an oligonucleotide probe, a polymerase and an inhibitor to the reaction. The inhibitor binds to the detector and the energy emitted as fluorescence emitted by the first fluorophore is transferred to the second fluorophore and emitted as fluorescence characteristic of the second fluorophore. If the oligonucleotide probe finds a match in the target nucleic acid, the polymerase will extend the probe until it reaches the inhibitor and displaces the inhibitor from the detector. As a result, the second fluorophore no longer has the transferred energy from the first fluorophore and, hence, no longer emits fluorescence. Accordingly, the fluorescence emitted is no longer characteristic of the second fluorophore and is once again characteristic of the first fluorophore. If the oligonucleotide probe does not find a match in the target nucleic acid, the inhibitor will remain in place and the fluorescence emitted will continue to be that characteristic of the second fluorophore.

In another embodiment of the methods of this invention, the detector is conjugated to a fluorophore and the inhibitor is conjugated to biotin ("inhibitor-biotin conjugate"), as illustrated in FIG. 7. In this example, the detector is incorporated into the target nucleic acid, followed by addition of an oligonucleotide probe, a polymerase and an inhibitor-biotin conjugate to the reaction. If the oligonucleotide probe finds a match in the target nucleic acid, the polymerase will extend the probe until it reaches the inhibitor-biotin conjugate and displaces the inhibitor-biotin conjugate from the detector. If the oligonucleotide probe does not find a match in the target nucleic acid, the inhibitor-biotin conjugate will remain in place. After the reaction is complete, inhibitor-biotin conjugate can be extracted from the reaction using a streptavidin substrate, e.g., streptavidin beads (readily available from various commercial vendors, e.g., Invitrogen, Solulink, Thermo Scientific and others), which will bind to the biotin of the inhibitor-biotin conjugate. In the case of a probe mismatch, where the inhibitor-biotin conjugate was not displaced from the detector by the probe, the streptavidin beads will extract a detector-inhibitor-biotin conjugate pair from the reaction. In the case of a probe match, where the inhibitor-biotin conjugate was displaced by the probe, the streptavidin beads will extract unbound inhibitor-biotin conjugate. A fluorescent signal emitted from the extracted sample is indicative of the presence of a detector-inhibitor-biotin conjugate pair and, hence, a probe mismatch, i.e., the absence of a target nucleic acid sequence. A relatively low fluorescent signal emitted from the extracted sample is indicative the absence of a detector and, hence, a probe match, i.e., the presence of a target nucleic acid sequence.

In another embodiment of the methods of this invention, the inhibitor may be conjugated to an epitope, e.g., an antigen, peptide or protein ("inhibitor-epitope conjugate"). In this example, the detector is incorporated into the target nucleic acid as described previously, followed by addition of an oligonucleotide probe, a polymerase, and inhibitor-epitope conjugate to the reaction. If the oligonucleotide probe finds a match in the target nucleic acid, the polymerase will extend the probe until it reaches the inhibitor-epitope conjugate and displaces the inhibitor-epitope conjugate from the detector. If the oligonucleotide probe does not find a match in the target nucleic acid, the inhibitor-epitope conjugate will remain in place on the detector. After the reaction is complete, the target nucleic acid can be purified to remove any unmatched probe and any unbound inhibitor-epitope conjugate from the reaction. After purification, the target nucleic acid is reacted with an antibody specific for the epitope. The antibody is conjugated to a detection system, e.g., a fluorescently labeled protein, or detected using a horseradish peroxidase ("HRP") assay (HRP chemiluminescent assays are commercially available from various vendors, e.g., Sigma-Aldrich, Invitrogen™, Thermo Scientific, Bio-Rad Laboratories, Inc., Cell Signaling Technology, Inc., Invitrogen™, and Biological Industries). The detection of an epitope signal indicates the presence of the inhibitor-epitope conjugate bound to the detector and, hence, a probe mismatch, i.e., the absence of a target nucleic acid sequence. A relatively low epitope signal indicates that the inhibitor-epitope conjugate is not bound to the detector and, hence, a probe match, i.e., the presence of a target nucleic acid sequence.

Figure 6:
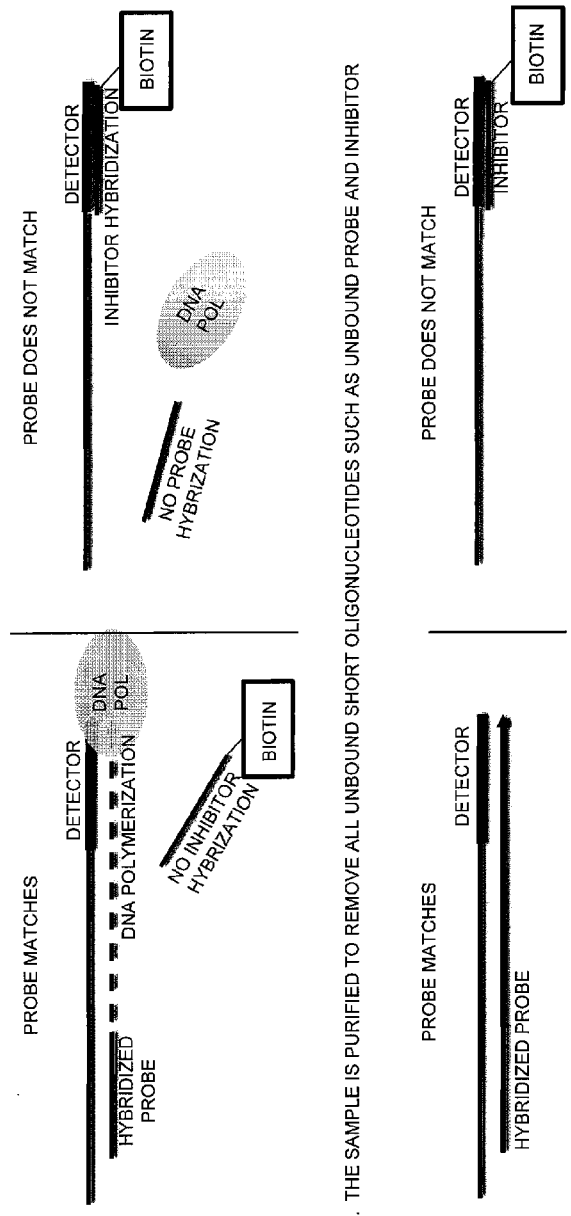
FIG. 6 is a schematic illustrating the example where the inhibitor is conjugated to biotin and a Horseradish Peroxidase chemiluminescence assay is used as the read-out mechanism.

FIG. 6 illustrates an example where the inhibitor is conjugated to an epitope wherein the inhibitor-epitope conjugate may comprise biotin as the epitope. In this example, the reaction proceeds as above and, after purification, the target nucleic acid is tested for the presence of inhibitor bound to the target nucleic acid by quantifying the amount of biotin remaining in the assay. For example, the remaining biotin may be detected by using an anti-biotin, HRP-linked antibody in a chemiluminescent assay, as described previously.

The results of the detection methods of this invention, referred to herein as "data", associated with a particular target nucleic acid sequence may then be kept in an accessible database, and may or may not be associated with other data from that particular human or animal associated with the target nucleic acid sequence or with data from other humans or animals. Data obtained may be stored in a database that can be integrated or associated with and/or cross-matched to other databases.

The methods and kits of this invention may further be associated with a network interface. The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The methods and kits of this invention may further provide for detecting a target nucleic acid sequence in a nucleic acid sample within an emulsion. An "emulsion", as used herein, is a stable mixture of at least two immiscible or partially immiscible liquids. In general, immiscible liquids tend to separate into two distinct phases. Accordingly, a surfactant may be added to stabilize the emulsion by reducing surface tension between the at least two immiscible or partially immiscible liquids and/or to stabilize the interface. For example, an emulsion according to the methods and kits of this invention may comprise a plurality of aqueous droplets in an immiscible oil, such as fluorocarbon oil, silicon oil or hydrocarbon oil where the droplet size ranges from about 0.5 to 5000 microns in diameter. A "droplet", as used herein, means an isolated aqueous or lipophilic phase within a continuous phase having any shape, for example but not limited to, cylindrical, spherical and ellipsoidal, as well as flattened, stretched or irregular shapes and so on.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

In this example, an assay was performed whereby a detector conjugated with a FAM fluorophore and incorporated into a target nucleic acid, was incubated at 34 C for 10 minutes in the presence of an inhibitor conjugated with an Iowa Black FQ quencher (Integrated DNA Technologies, Inc.), Manta DNA polymerase (Enzymatics®), dNTPs, the appropriate buffer (supplied with the DNA polymerase from Enzymatics®) and a short oligonucleotide probe having either an exact match to the target nucleic acid or a single position mismatch at one of 6 different positions along the 8 nucleotide long probe as illustrated in FIG. 8.

Figure 9:
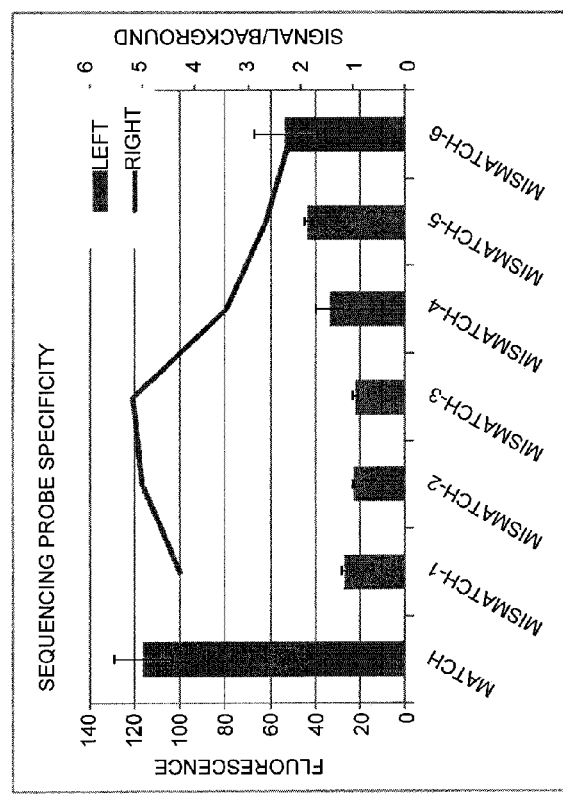
FIG. 9 shows the fluorescence measured for samples containing either the match probe or one of 6 mismatch probes using a microplate reader for the 7 reactions of Example 1.

Fluorescence was measured using a microplate reader for the 7 reactions. As illustrated in FIG. 9, fluorescence in the sample containing a matched probe was 2 to 5 fold higher than in samples containing mismatched probes.

Example 2

Figure 10:
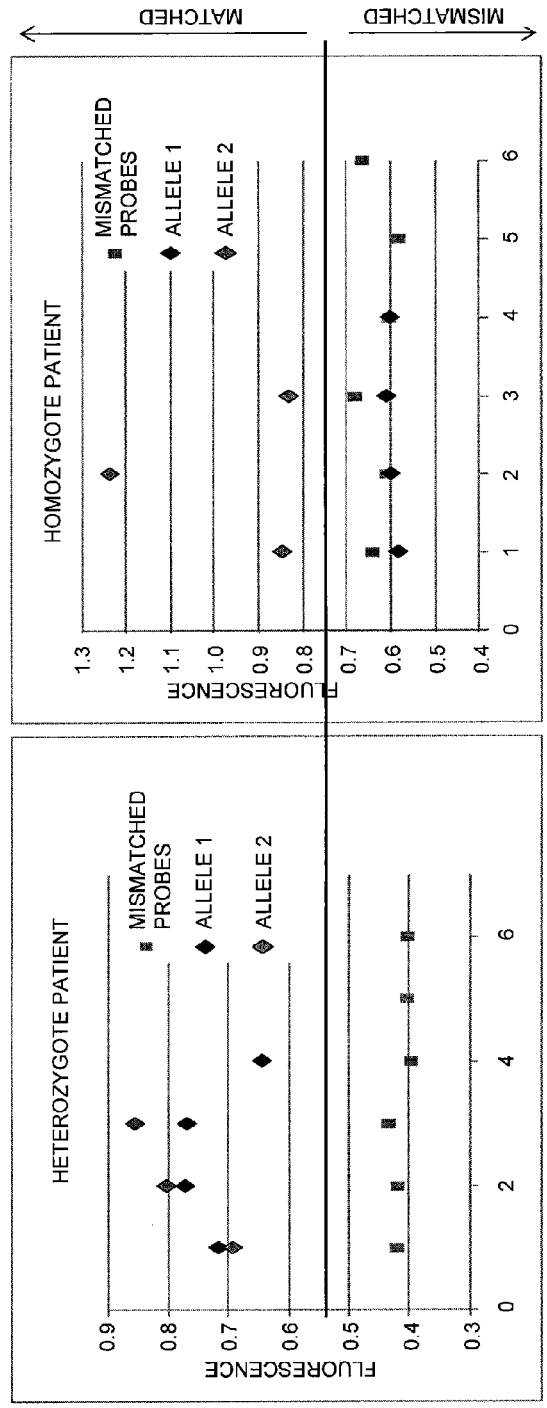
FIG. 10 shows the fluorescence measured in samples from a heterozygote and a homozygote patient using probes to distinguish between 2 different alleles of the TNNT2 gene, as described in Example 2.

In this example, an assay was performed wherein a set of oligonucleotide probes was used to distinguish between 2 different alleles in patient samples. The TNNT2 gene was first PCR amplified (exons 4-5, 477 bp) using genomic DNA from one patient who was a heterozygote for an A/G SNP and another patient who was a homozygote (G). One of the PCR primers (forward) was labeled with a FAM fluorophore (Integrated DNA Technologies, Inc.). The PCR the samples were converted to single stranded DNA and mixed with an inhibitor conjugated to the Iowa Black® FQ quencher (Integrated DNA Technologies, Inc.), Manta DNA polymerase (Enzymatics®), dNTPs, the appropriate buffer (supplied with the enzyme from Enzymatics®), and a short probe that either matched the SNP allele (allele 1), the "WT" allele (allele 2) or did not match the target (i.e., it was a randomly chosen from a library of hexamer probes). The fluorescence of each sample was measured after incubation for 30 minutes at 34° C. As illustrated in FIG. 10, relatively high fluorescence is seen with probes matching both alleles 1 and 2 for the heterozygous patient but only allele 2 for the homozygous patient, and relatively low fluorescence is also seen for all mismatched probes.

Example 3

Figure 11:
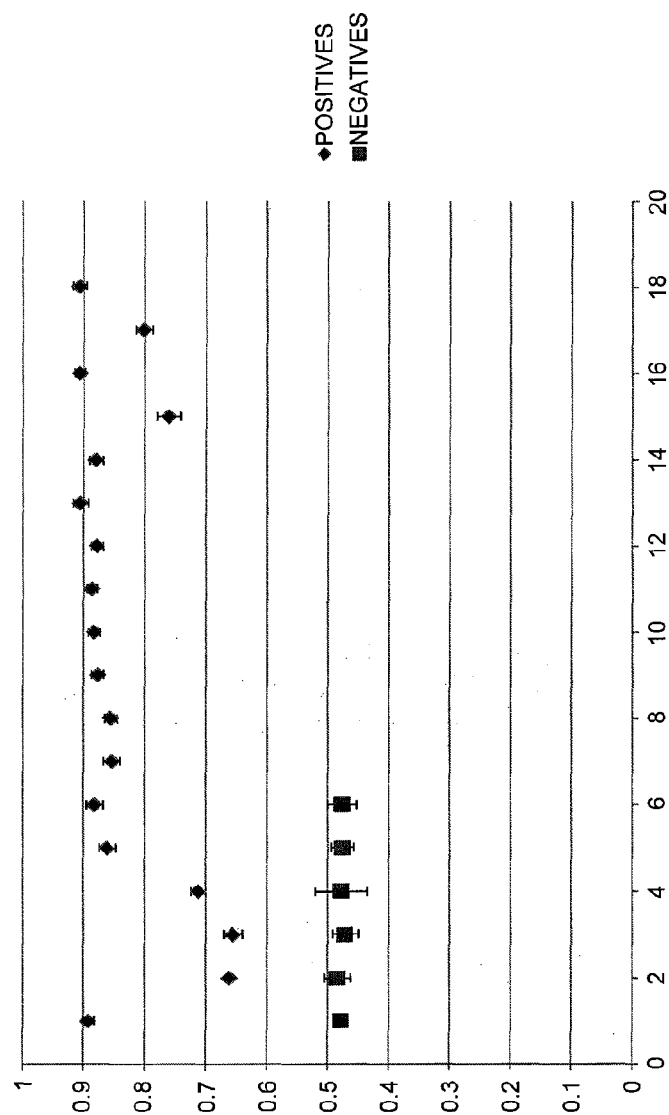
FIG. 11 shows the average fluorescence and standard deviations for each probe match and mismatch probe types used to analyze the target nucleic acid of Example 3.

In this example, a 191 bp single stranded DNA amplicon containing a detector conjugated to a FAM fluorophore (Integrated DNA Technologies, Inc.) was incubated for 30 minutes at 34° C. and then combined with an inhibitor conjugated to the Iowa Black® FQ quencher (Integrated DNA Technologies, Inc.), Manta DNA polymerase (Enzymatics®), dNTPs, the appropriate buffer (supplied with the enzyme from Enzymatics®), and one of 24 short probes (6 to 8 nucleotide long) that either exactly matched the target (18 probes) or was a mismatch (6 probes). Each one of the 24 mixtures was emulsified into picoliter sized droplets, after which fluorescence was detected for thousands of emulsified drops (1700 drops were measured for each probe on average). The average fluorescence of each probe type and the standard deviations are shown in FIG. 11. Mismatched probes (negatives) all have low fluorescence and all matched probes (positives) have high fluorescence (bars=standard deviation).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for detecting a target nucleic acid comprising:
   a) incorporating a detector oligonucleotide conjugated to a fluorophore or a quencher into a target nucleic acid to form a reaction, said incorporating comprising:
      i. ligation; or
      ii. by amplification using a PCR primer comprising (i) a target-specific sequence on the 3' end of the primer (ii) a universal nucleic acid sequence complementary to the inhibitor and (iii) the fluorophore or quencher;
   b) adding an oligonucleotide probe to the reaction;
   c) adding an inhibitor oligonucleotide to the reaction such that the inhibitor oligonucleotide hybridizes to the incorporated detector, wherein the inhibitor oligonucleotide is conjugated to a quencher if the detector oligonucleotide is conjugated to a fluorophore and wherein the inhibitor oligonucleotide is conjugated to a fluorophore if the detector oligonucleotide is conjugated to a quencher and wherein hybridization of the inhibitor oligonucleotide to the detector oligonucleotide quenches signal from the fluorophore; and
   d) detecting interference of the oligonucleotide probe with the inhibitor oligonucleotide as an indication of the presence of the target nucleic acid, thereby detecting a target nucleic acid, wherein the detecting comprises performing a strand displacement reaction with a polymerase that extends the oligonucleotide probe, displaces the inhibitor oligonucleotide, and no longer quenches the fluorophore to generate a fluorescent signal if the oligonucleotide probe hybridizes to the target nucleic acid.

2. A method according to claim 1, wherein the target nucleic acid is single stranded.

3. A method according to claim 1, wherein a single nucleotide within the target nucleic acid is detected.

4. A method according to claim 1, wherein a sequence of 6-8 nucleotides within the target nucleic acid is detected.

5. A method according to claim 1, wherein the entire target nucleic acid is detected.

6. A method according to claim 1, wherein a variance within the target nucleic acid is detected.

7. A method according to claim 1, wherein a mutation within the target nucleic acid is detected.

8. A method according to claim 1, wherein a polymorphism within the target nucleic acid is detected.

9. A method according to claim 1, wherein the detector oligonucleotide is conjugated to a fluorophore.

10. A method according to claim 1, wherein the inhibitor oligonucleotide is conjugated to a quencher.

11. A method according to claim 1, wherein the detector oligonucleotide is conjugated to a quencher.

12. A method according to claim 1, wherein the inhibitor oligonucleotide is conjugated to a fluorophore.

13. A method according to claim 1, wherein the detector oligonucleotide is conjugated to an epitope.

14. A method according to claim 1, wherein the inhibitor is conjugated to an epitope.

15. A method according to claim 1, wherein more than one target nucleic acid is detected.

16. A method according to claim 1, wherein the method takes place within an emulsion.

17. A method according to claim 16, wherein the emulsion is in a microfluidic device.

18. The method of claim 1, wherein the detector oligonucleotide has a 5' end and the fluorophore or quencher is conjugated to the 5' end of the detector oligonucleotide.

19. The method of claim 1, wherein the incorporating comprises ligation.

20. The method of claim 1, wherein the incorporating comprises amplification using a PCR primer comprising a target-specific sequence on the 3' end of the primer and a universal nucleic acid sequence complementary to the inhibitor on the 5' end of the primer.

* * * * *

SEQUENCE LISTING

```
<160> NUMBER OF SEQ ID NOS: 7

<210> SEQ ID NO 1
<211> LENGTH: 8
<212> TYPE: DNA
<213> ORGANISM: Artificial Sequence
<220> FEATURE:
<223> OTHER INFORMATION: Commercially available plasmid DNA, Puc19
      vector

<400> SEQUENCE: 1 cgcatatg                                                               8

<210> SEQ ID NO 2
<211> LENGTH: 8
<212> TYPE: DNA
<213> ORGANISM: Artificial Sequence
<220> FEATURE:
<223> OTHER INFORMATION: Commercially available plasmid DNA, Puc19
      vector

<400> SEQUENCE: 2 cgcatatc                                                               8

<210> SEQ ID NO 3
<211> LENGTH: 8
<212> TYPE: DNA
<213> ORGANISM: Artificial Sequence
<220> FEATURE:
<223> OTHER INFORMATION: Commercially available plasmid DNA, Puc19
      vector

<400> SEQUENCE: 3 cgcatagg                                                               8
```

```
<210> SEQ ID NO 4
<211> LENGTH: 8
<212> TYPE: DNA
<213> ORGANISM: Artificial Sequence
<220> FEATURE:
<223> OTHER INFORMATION: Commercially available plasmid DNA, Puc19
      vector

<400> SEQUENCE: 4 cgcatctg                                                                   8

<210> SEQ ID NO 5
<211> LENGTH: 8
<212> TYPE: DNA
<213> ORGANISM: Artificial Sequence
<220> FEATURE:
<223> OTHER INFORMATION: Commercially available plasmid DNA, Puc19
      vector

<400> SEQUENCE: 5 cgcagatg                                                                   8

<210> SEQ ID NO 6
<211> LENGTH: 8
<212> TYPE: DNA
<213> ORGANISM: Artificial Sequence
<220> FEATURE:
<223> OTHER INFORMATION: Commercially available plasmid DNA, Puc19
      vector

<400> SEQUENCE: 6 cgcctatg                                                                   8

<210> SEQ ID NO 7
<211> LENGTH: 8
<212> TYPE: DNA
<213> ORGANISM: Artificial Sequence
<220> FEATURE:
<223> OTHER INFORMATION: Commercially available plasmid DNA, Puc19
      vector

<400> SEQUENCE: 7 cggatatg                                                                   8
```